United States Patent [19]

Strege et al.

[11] 4,344,881

[45] Aug. 17, 1982

[54] PROCESS FOR MAKING ALKYLENE CARBONATES

[75] Inventors: Paul E. Strege; James M. Renga, both Midland, Mich.

[73] Assignee: The Dow Chemical Company, Midland, Mich.

[21] Appl. No.: 230,212

[22] Filed: Feb. 2, 1981

[51] Int. Cl.$^3$ .................. C07D 317/38; C07D 317/36
[52] U.S. Cl. ..................................... 549/229; 549/230
[58] Field of Search ..................................... 260/340.2

[56] References Cited

U.S. PATENT DOCUMENTS 4,061,664 12/1977 Wood ................................. 260/338

FOREIGN PATENT DOCUMENTS 1336787 11/1973 United Kingdom .

OTHER PUBLICATIONS

Carl R. Noller, Chemistry of Organic Compounds, 2nd ed. (1957), pp. 310 and 741.
Kadaba et al., J. Org. Chem., 25, 1431–1433 (1960).

*Primary Examiner*—Norma S. Milestone
*Attorney, Agent, or Firm*—David H. Thurston; Douglas N. Deline

[57] ABSTRACT

A lower alkyl trichloroacetate and a vicinal alkylene diol react when heated together in the presence of a weak base to produce chloroform, a lower alkanol, and the cyclic alkylene carbonate. The chloroform and lower alkanol distill from the reaction mixture substantially as formed and the alkylene carbonate is readily separable from the residual mixture.

11 Claims, No Drawings

PROCESS FOR MAKING ALKYLENE CARBONATES

BACKGROUND OF THE INVENTION

This invention relates to a new chemical process, more particularly, to a new method for the production of cyclic alkylene carbonates.

In the past, cyclic alkylene carbonates such as ethylene carbonate and propylene carbonate have been made by methods such as the reaction of a glycol with phosgene, the transesterification reaction of a glycol with a dialkyl carbonate, and the addition of $CO_2$ to an epoxide. Alkylene carbonates have also been made by the reaction of a glycol with carbon monoxide and oxygen although the reported yields have been relatively low.

It is known that an alkyl trichloroacetate reacts with an alcohol in the presence of a weakly basic compound to produce the corresponding dialkyl carbonate and a mole of chloroform, see Praetorius et al., British Patent No. 1,336,787.

SUMMARY OF THE INVENTION

It has now been found that when a mixture of an alkyl trichloroacetate and a vicinal alkylene diol is heated at 100° C.–250° C. in the presence of a small but effective amount of a base selected from the group consisting of an alkali metal alkoxide, a salt of a strong base and a weak acid, and a non-nucleophilic organic base, a reaction takes place with the formation of chloroform and an alkanol plus the cyclic alkylene carbonate according to the equation:

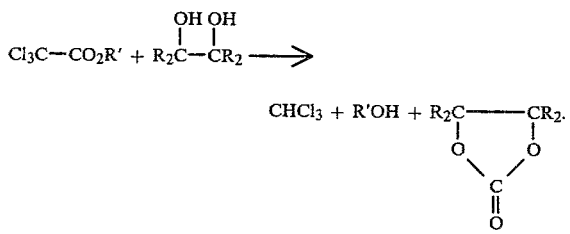

In the above equation, R' is an alkyl group of 1–6 carbon atoms, preferably a lower alkyl group, and each R represents hydrogen, an alkyl group of 1–8 carbon atoms, a cycloalkyl group of 5–7 carbon atoms, a chloromethyl group, or an aromatic group.

Under the reaction conditions, the volatile chloroform and alkanol coproducts distill from the reaction mixture and the residual reaction mixture then consists essentially of the alkylene carbonate plus the basic catalyst and any unreacted starting material. The pure alkylene carbonate is readily separable by distillation or other conventional means.

DETAILED DESCRIPTION OF THE INVENTION

Preferably, the alkylene diol and alkyl trichloroacetate reactants are employed in essentially molar equivalent amounts so that the reacted mixture is substantially the alkylene carbonate product plus the small amount of catalyst used, thereby simplifying the separation of pure alkylene carbonate. An excess of either reactant can be employed, but no advantage in the reaction is thereby gained and the production of by-products, such as the glycol bis(trichloroacetate) or the hydroxyalkyl trichloroacetate increases accordingly.

The basic catalyst for the reaction can be an alkali metal alkoxide, a salt of a strong base and a weak acid, or a non-nucleophilic organic base. The latter class consists in practice of tertiary amines, both aliphatic and aromatic. Thus amines such as triethylamine, tributylamine, pyridine, quinoline, and (N,N-dimethylamino)-pyridine are suitable catalysts for the reaction and metal compounds such as sodium carbonate, potassium carbonate, sodium acetate, potassium alkoxide, and other such alkali metal compounds are also effective for the purpose. An alkoxide catalyst can be formed in situ by addition to the reaction mixture of a portion of alkali metal which then reacts with the diol reactant and probably later with the alkanol by-product of the reaction, in either case to make a corresponding alkoxide. The quantity of basic catalyst is not a critical factor so long as any significant amount is present. Normally, about 0.01–1 percent of basic catalyst based on the weight of reactants is preferred. Larger amounts of catalyst can be used but may complicate the final separation of a good yield of pure product.

The catalyst should be at least partially soluble in the reaction mixture and when an inorganic catalyst such as an alkali metal carbonate is used, it is advantageous to use a phase-transfer catalyst in conjunction with it, for example, the cyclic oligomers of ethylene oxide known as crown ethers. Such phase-transfer catalysts can be used in minor amounts, for example, about 0.005–0.1 mole per mole of basic catalyst is effective. A reaction solvent can also be used if desired although this is not usually the case. Glycol ethers and other ethers of appropriate boiling point are suitably inert reaction solvents.

Substantially any alkyl trichloroacetate can be used in the process, but a lower alkyl trichloroacetate reactant such as a methyl, ethyl, or butyl ester is preferred. The methyl and ethyl trichloroacetates are generally most preferred because of the lower boiling alkanol coproduct thereby produced.

As defined by the above structural formula, the diol reactant can be substantially any vicinal diol free of interfering reactive substituents. Such diols include the simple alkylene diols ethylene glycol, propylene glycol, and butylene glycol; also substituted glycols such as 3-methoxy-1,2-propanediol, 3-chloro-1,2-propanediol, styrene glycol, cyclohexylethylene glycol, 1,2-hexanediol, and the like.

The reaction temperature is a critically important factor in this reaction, for too low a temperature causes incomplete reaction with the production of glycol trichloroacetate esters rather than the cyclic alkylene carbonate. A reaction temperature of about 120° C.–180° C. is preferred in order to obtain complete reaction in a relatively short reaction time with removal by distillation of the chloroform and alkanol coproducts from the reaction mixture substantially as they are formed. Under preferred conditions the reaction time ordinarily is about 0.1–5 hours.

In the usual operation of the process, equal molar proportions of the alkyl trichloroacetate and diol reactants are combined with a small amount of basic catalyst as previously defined in a reactor flask or other vessel equipped with a distillation head and the reaction mixture is heated, preferably to about 120° C.–180° C. as noted above. The chloroform and alkanol products then distill off substantially as formed and the progress of the reaction can be followed by noting the quantity of these products distilled from the reactor and collected as condensate in a suitable receiver. After the reaction has been substantially completed, the residual reaction mixture consists essentially of the alkylene carbonate and the basic catalyst. Purified alkylene carbonate can be obtained in high yield by distillation of this residual mixture or by other conventional purification means. The process has the advantages of high yields and the absence of any waste acid or salt by-products, the only other products being the useful solvents chloroform and lower alkanol.

The cyclic alkylene carbonate products are more accurately named according to the IUPAC system as 1,3-dioxol-2-ones with any substituents in the 4 and 5 positions. Both the common names and the IUPAC names are used to designate the products in the examples.

EXAMPLE 1

A mixture of 4.86 g (0.0784 g mole) ethylene glycol and 15 g (0.0784 g mole) ethyl trichloroacetate was heated at 160° C. for five hours in the presence of a small piece (about 0.05 g) of metallic sodium. Chloroform and ethyl alcohol distilled from the reaction mixture and were collected by means of a distillation head connected to the reaction flask. The crude residual product was purified by distillation to obtain 5.15 g of ethylene carbonate (1,3-dioxol-2-one), a yield of 75 percent based on the starting reactants.

EXAMPLE 2

The procedure of Example 1 was repeated using the same molar quantity of propylene glycol in place of the ethylene glycol to obtain 6.05 g of distilled propylene glycol (4-methyl-1,3-dioxol-2-one), a yield of 76 percent.

EXAMPLE 3

As described in Example 1, the same quantities of ethylene glycol and ethyl trichloroacetate were heated for 1.5 hours at 160° C. in admixture with 0.03 g of $K_2CO_3$ and 0.01 g of 18-crown-6. The residual reaction mixture remaining after distillation of the chloroform and ethyl alcohol by-products was distilled to obtain 6.2 g of ethylene carbonate representing a 90 percent yield.

EXAMPLE 4

Example 3 was repeated using the same molar quantity of propylene glycol in place of the ethylene glycol reactant. A yield of 6.8 g distilled propylene carbonate was obtained, 85 percent of the theoretical amount.

EXAMPLE 5

Similarly, a mixture of 4.86 g of ethylene glycol, 15 g of ethyl trichloroacetate, and 0.1 g of 4-(N,N-dimethylamino)pyridine was heated at 160° C. for three hours with removal by distillation of chloroform and ethyl alcohol. Distillation of the residual reaction mixture yielded 6.25 g of ethylene carbonate, 91 percent of the theoretical amount.

EXAMPLE 6

Example 5 was repeated using the same molar quantity of 2,3-butanediol in place of ethylene glycol, and the reaction mixture was heated to 120° C. for thirty minutes, then to 150° C. for an additional thirty minutes. A yield of 8.0 g distilled 4,5-dimethyl-1,3-dioxol-2-one was obtained, 88 percent of the theoretical amount.

EXAMPLE 7

Example 5 was repeated using the same molar quantity of 3-chloro-1,2-propanediol in place of ethylene glycol, and the reaction mixture was heated to 120° C. for sixty minutes, then to 150° C. for an additional thirty minutes. A yield of 8.8 g distilled (4-chloromethyl)-1,3-dioxol-2-one was obtained, 82 percent of the theoretical amount.

In the manner described in the above examples, styrene glycol (1-phenyl-1,2-ethanediol) is reacted with ethyl trichloroacetate in the presence of $K_2CO_3$ or other basic catalyst as defined herein to make 1-phenylethylene carbonate (4-phenyl-1,3-dioxol-2-one), 1-cyclohexyl-1,2-ethanediol is reacted with methyl trichloroacetate to make 1-cyclohexylethylene carbonate (4-cyclohexyl-1,3-dioxol-2-one), and 1,2-hexanediol is reacted with ethyl trichloroacetate to make 1,2-hexylene carbonate (4-butyl-1,3-dioxol-2-one).

We claim:

1. A process for making a cyclic alkylene carbonate which comprises heating a mixture of a lower alkyl trichloroacetate with about a molar equivalent of a vicinal alkylene diol in the presence of a small but effective amount of a base selected from the group consisting of an alkali metal alkoxide, a salt of a strong base and a weak acid, and a non-nucleophilic organic base at about 100° C.–250° C., thereby causing the formation and substantial distillation of chloroform and lower alkanol from said mixture and separating the alkylene carbonate product from the residual mixture.

2. The process of claim 1 wherein the alkylene diol is ethylene glycol.

3. The process of claim 1 wherein the alkylene diol is propylene glycol.

4. The process of claim 1 wherein the alkylene diol is 3-(chloromethyl)-1,2-propanediol.

5. The process of claim 1 wherein the alkylene diol is 2,3-butanediol.

6. The process of claim 1 wherein the base is an alkali metal carbonate.

7. The process of claim 6 wherein a crown ether is included in the reaction mixture as a phase-transfer catalyst.

8. The process of claim 1 wherein the reaction temperature is about 120° C.–180° C.

9. The process of claim 1 wherein the base is a non-nucleophilic organic base.

10. The process of claim 9 wherein the organic base is a tertiary amine.

11. The process of claim 1 wherein the base is an alkali metal alkoxide.